US010143357B2

(12) United States Patent
Yamada

(10) Patent No.: US 10,143,357 B2
(45) Date of Patent: Dec. 4, 2018

(54) ENDOSCOPE GRIPPING DEVICE

(75) Inventor: Ronald Yamada, Manteca, CA (US)

(73) Assignee: Ronald Yamada, Manteca, CA (US)

( * ) Notice: Subject to any disclaimer, the term of this patent is extended or adjusted under 35 U.S.C. 154(b) by 0 days.

(21) Appl. No.: 12/806,378

(22) Filed: Aug. 10, 2010

(65) Prior Publication Data

US 2012/0041260 A1    Feb. 16, 2012

(51) Int. Cl.
*A61B 1/00* (2006.01)
*F16K 7/00* (2006.01)
*F16K 7/02* (2006.01)
*F16K 7/04* (2006.01)
*A61M 39/28* (2006.01)

(52) U.S. Cl.
CPC ........ *A61B 1/00131* (2013.01); *A61B 1/0014* (2013.01); *A61B 1/00066* (2013.01); *A61B 1/00101* (2013.01); *A61B 1/00133* (2013.01); *A61B 1/00147* (2013.01); *A61M 39/28* (2013.01); *F16K 7/00* (2013.01); *F16K 7/02* (2013.01); *F16K 7/04* (2013.01)

(58) Field of Classification Search
CPC ............ A61B 1/00066; A61B 1/00101; A61B 1/00121; A61B 1/00131; A61B 1/00133; A61B 1/0014; A61B 1/00147; A61B 1/01; F16K 7/00; F16K 7/02; F16K 7/04; F16K 7/045; F16K 7/06; F16K 7/061; F16K 7/063; F16K 7/065; F16K 7/066; F16K 7/068; F16K 7/07; F16K 7/075; F16K 7/08; F16K 7/10; F16K 7/12; F16K 7/123; F16K 7/1236; F16K 7/14; F16K 7/16; F16K 7/17; F16K 7/18; F16K 7/20

USPC .... 606/209, 1; 600/102, 114, 106–107, 119, 600/131
See application file for complete search history.

(56) References Cited

U.S. PATENT DOCUMENTS

| 3,194,452 | A | * | 7/1965 | Sanderford | A61M 1/0078 222/102 |
| 3,648,701 | A | * | 3/1972 | Botts | A61M 1/0078 251/6 |
| 3,727,605 | A |   | 4/1973 | Klein | |
| 4,164,223 | A | * | 8/1979 | Munib | A61M 1/0078 24/115 L |
| 4,453,295 | A | * | 6/1984 | Laszczower | A61M 39/284 24/115 G |
| 4,834,702 | A | * | 5/1989 | Rocco | A61B 17/22 251/4 |
| 5,071,102 | A | * | 12/1991 | Gray | F16K 7/063 251/4 |
| 5,273,252 | A | * | 12/1993 | Brugalieres | F16L 55/10 251/9 |

(Continued)

FOREIGN PATENT DOCUMENTS

JP    9094219    4/1997

*Primary Examiner* — Ryan Henderson
(74) *Attorney, Agent, or Firm* — Haynes and Boone, LLP

(57) ABSTRACT

A gripping device for an endoscope insertion tube utilizing first and second arms that are hingedly attached to one another. Each arm includes an opening to accommodate the insertion tube of an endoscope such that the endoscope insertion tube spans both arms. First and second jaws are associated with first and second arms and are positioned in opposition to one another. The movement of the arms toward one anther causes the jaws to engage the insertion tube which is guided through the arms by the apertures found in the arms.

10 Claims, 3 Drawing Sheets

(56) References Cited

U.S. PATENT DOCUMENTS

| | | | |
|---|---|---|---|
| 5,441,042 A | 8/1995 | Putman | |
| 5,586,553 A | 12/1996 | Halili et al. | |
| 5,667,068 A | 9/1997 | Weaver | |
| 5,667,514 A | 9/1997 | Heller | |
| 5,702,349 A | 12/1997 | Morizumi | |
| 5,741,284 A | 4/1998 | Karlsson | |
| 6,540,737 B2 | 4/2003 | Bacher et al. | |
| 6,679,834 B2 | 1/2004 | Stahl et al. | |
| 6,966,876 B2 | 11/2005 | Irion et al. | |
| 6,976,955 B2 | 12/2005 | Hardin et al. | |
| 7,413,543 B2 * | 8/2008 | Banik et al. | 600/129 |
| 7,520,185 B2 | 4/2009 | Baldewein et al. | |
| 7,559,525 B2 * | 7/2009 | Grimes | F16K 7/063 251/8 |
| 7,998,168 B2 * | 8/2011 | Kleimann, Sr. | B08B 9/027 137/15.04 |
| 8,287,654 B2 * | 10/2012 | Shaffer | A61M 25/00 134/16 |
| 8,356,791 B1 * | 1/2013 | Blom | F16K 7/06 251/4 |
| 8,387,655 B2 * | 3/2013 | Cowlishaw | F16K 7/06 137/512 |
| 8,657,866 B2 * | 2/2014 | Melsheimer | A61F 2/064 606/908 |
| 9,101,482 B2 * | 8/2015 | Rondeau | A61F 5/445 |
| 9,421,602 B2 * | 8/2016 | Hawkes | B21H 7/16 |
| 2003/0139769 A1 * | 7/2003 | Schrader et al. | 606/209 |
| 2004/0267305 A1 * | 12/2004 | Borgman | 606/209 |
| 2005/0070852 A1 | 3/2005 | Wright | |
| 2005/0256371 A1 | 11/2005 | Schara et al. | |
| 2005/0256375 A1 | 11/2005 | Freed | |
| 2009/0247827 A1 | 10/2009 | Secrest et al. | |

* cited by examiner

ENDOSCOPE GRIPPING DEVICE

BACKGROUND OF THE INVENTION

The present invention relates to a novel and useful endoscope gripping device.

Endoscopes are medical devices used to examine the inside a person's body and each generally includes of a long, thin, flexible (or rigid) insertion tube. The terminus of the endoscope tube also is provided with a light and a video camera. Images of the inside of a patient's body are then projected onto a screen. Thus, an endoscope may be used to examine the interior surfaces of an organ or tissue within the body cavity. In addition, the endoscope may also be employed for enabling biopsies and retrieving foreign objects, generally in the gastrointestinal tract.

Practitioners employing endoscopes during endoscopy procedures are susceptible to overuse injuries occurring from repeated microtrauma to a tendon, ligament, or joint, or repeated ischemia to peripheral nerves.

During the endoscopy procedure, the practitioner normally uses the left hand to grip and stabilize the control system such that the left thumb manipulates the control dials. The right hand pinches or grips the insertion tube and the right arm pushes, pulls, and applies torque to the endoscope. Such maneuvers involve the application of relatively high forces by the practitioner. As a consequence, these activities require extreme or prolonged wrist flexion or extension, and radial or ulnar deviation. The combination of high finger forces with awkward wrist postures exacerbates the risk of overuse injury to the practitioner.

In the past, many systems have been proposed for the insertion of medical devices and probes, such as endoscopes. For example, U.S. Pat. No. 7,520,185 shows a sensor handle assembly for implantation into a body part that carries a force indicator.

U.S. Pat. No. 5,667,514 shows a device for inserting a flexible element into a soft tissue which includes a pair of tubular portions defining a lumen for a surgical tool. The pair of tubular members each includes slits that may be aligned later to allow the withdrawal of the surgical tube without interfering with the inserted surgical instrument.

U.S. Pat. Nos. 5,667,068 and 6,976,955, as well as United States Patent Publications 2005/0256375, and 2009/0247827, and Japanese Patent Publication No. JP 9094219 (A), describe cylindrical type handles that surround an endoscope tube, catheter, or other like device, to allow the practitioner to easily grip the probe being inserted into a body cavity.

U.S. Pat. No. 5,741,284 describes a dialyses probe which is maneuvered by the use of a handle having two upstanding parts and wings which enables canular tubes to be withdrawn using only two fingers of the practitioner.

United States Patent Publication 2005/0256371 illustrates a robotic endoscope holder which may maneuver the endoscope using electromechanical mechanisms.

U.S. Pat. Nos. 5,441,042, 5,702,349, and United States Patent Publication No. 2005/0070852 show clamping or adhesive holding devices for an endoscope tube for use during surgical procedures.

U.S. Pat. No. 6,966,876 teaches a device for holding and positioning an endoscope by the use of two bow-shaped elements which pivot and tend to guide the endoscope during insertion procedures.

U.S. Pat. Nos. 5,586,553 and 6,679,834 illustrate holders for an endoscope for a cannula which includes a base member that surrounds the tubular portion of the device and holds the same at an angle to the base member.

U.S. Pat. Nos. 3,727,605 and 6,540,737 describe elongated medical instrument holders which employ supports which allow the practitioner to indirectly grip an elongated medical instrument such as an endoscope when used to enter the body cavity.

A gripping device for an endoscope which greatly relieves stresses on the practitioners hand would be a notable advance in the medical field.

SUMMARY OF THE INVENTION

In accordance with the present invention a novel and useful endoscope gripping device is herein provided.

The endoscope gripping device of the present invention utilizes first and second arms that are pivotally connected to one another via a hinge. Each of the first and second arms includes an aperture which provides a guiding mechanism for an endoscope tube during endoscopy procedures.

Moreover, each of the pivotally arms also is provided with a jaw. The jaws are opposed to one another and are capable of squeezing or clamping the insertion tube when the first and second arms move toward one another. The first and second jaws may include recessed or concave surfaces that are fashioned to fit around the perimeter of the endoscope tube.

The device of the present invention, following insertion of the endoscope tube through the apertures of the pivoting first and second arms, permits the medical practitioner to release or grip the endoscope insertion tube, with the hand of the practitioner being located along the device in an unstressed position.

It may be apparent that a novel and useful gripping device for an insertion tube of an endoscope has been hereinabove described.

It is therefore an object of the present invention to provide a gripping device for an insertion tube of an endoscope which is simple and easy to use and relieves the stresses on the practitioners hand during endoscope maneuvering due to wrist flexion or extension or radial or ulnar deviation.

Another object of the present invention is to provide a gripping device for the insertion tube of an endoscope which may be readily adapted to use with a lubricated insertion tube of an endoscope and which is disposable following its use.

A further object of the present invention is to provide a gripping device for an endoscope that may be activated to firmly grip the insertion tube of the endoscope without slippage allowing the practitioner to insert, withdrawal, or torque the insertion tube during endoscopy procedures.

Another object of the present invention is to provide a gripping device for an endoscope which is relatively simple and economical to manufacture and is adaptable to endoscope tube of varying diameters.

A further object of the present invention is to provide a gripping device for an endoscope which eliminates carpal injuries or tendonitis in the hands of the medical practitioner during use over an extended time period.

The invention possesses other objects and advantages especially as concerns particular characteristics and features thereof which will become apparent as the specification continues.

For a better understanding of the invention reference is made to the following detailed description of the preferred embodiments of the invention which should be taken in conjunction with the above described drawings.

DETAILED DESCRIPTION OF THE PREFERRED EMBODIMENTS OF THE INVENTION

Various aspects of the present invention will evolve from the following detailed description of the preferred embodiments thereof which should be referenced to the prior described drawings.

Figure 1:
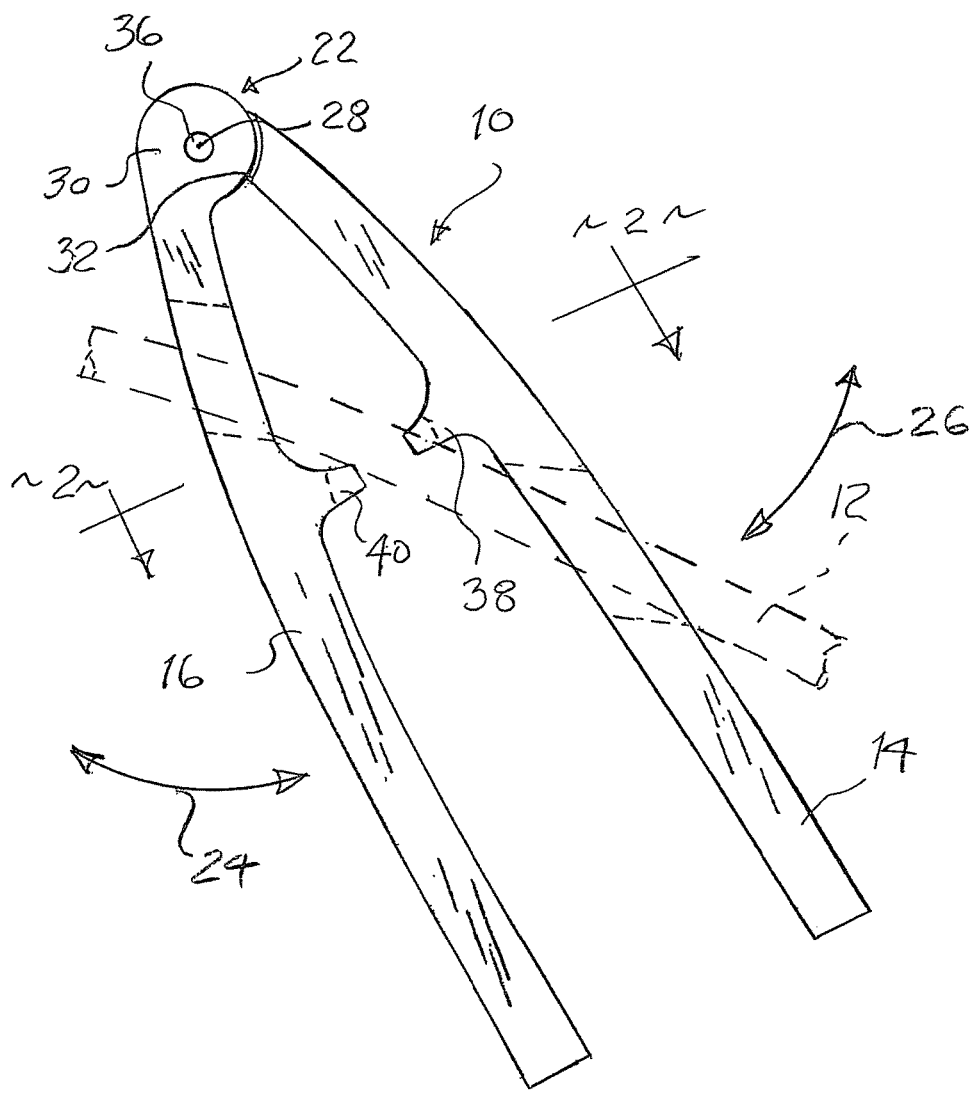
FIG. 1 is a side elevational view of the device of the present invention with an endoscope tube illustrated in phantom, positioned for tightening by the pair of jaws.

An embodiment of the present invention is depicted in the drawings by reference character 10. The gripping device 10 is intended for use with an insertion tube of an endoscope 12 which is direct into a body cavity by a medical practitioner. Insertion tube 12 is usually lubricated and may possess varying diameters. With reference to FIG. 1, it may be observed that gripping device 10 includes a first arm 14 and a second arm 16. First and second arms 14 and 16 are provided with apertures 18 and 20 to guide endoscope insertion tube 12 therethrough apertures 18 and 20 may be elongated and serve to guide insertion tube 12 in spanning arms 14 and 16. In this regard, endoscope insertion tube 12 is depicted in phantom on FIG. 1, and partially in FIGS. 2 and 5. Arms 14 and 16 may be formed of any suitable rigid or semi-rigid materials such as metal, wood, polymeric plastic, and the like.

A hinge 22 is also found in the device of the present invention. Hinge 22 rotatably connects first arm 14 to second arm 16 for movement according to directional arrows 24 and 26 of FIG. 1. That is to say, arms 14 and 16 may rotate towards or away from one another by rotational movement of hinged 22 about axis 28. Hinge 22 is formed with a slotted receiver 30 that lies at the terminus of second arm 16. A rounded head or tongue 32 fits within slot 34 of receiver 30 and lies at the terminus of first arm 14. Pivot pin 36, FIG. 1, penetrates slotted receiver 30 and tongue 32 and allows the rotational movement of arm 14 relative to arm 16, prior described.

Most notably, a first jaw is associated with and extends from first arm 14. Likewise, a second jaw 40 extends from, and is associated with second arm 16. Jaws 38 and 40 are essentially protuberances that are opposed to one another. First jaw 38 is provided with a concave surface 42, while second jaw possesses a concave surface 44. As shown in drawings, FIG. 2, concave surfaces 42 and 44 of jaws 38 and 40, respectively squeeze or clamp insertion tube 12 when arms 14 and 16 are moved toward one another. Such squeezing of jaws 38 and 40 prevents the movements of insertion tube 12 through apertures 18 and 20. Likewise, the movement of jaws 14 and 16 away from one another releases endoscope insertion tube 12 from device 10 and allows the practitioner to move the same in either direction through apertures 18 and 20, as desired.

Figure 2:
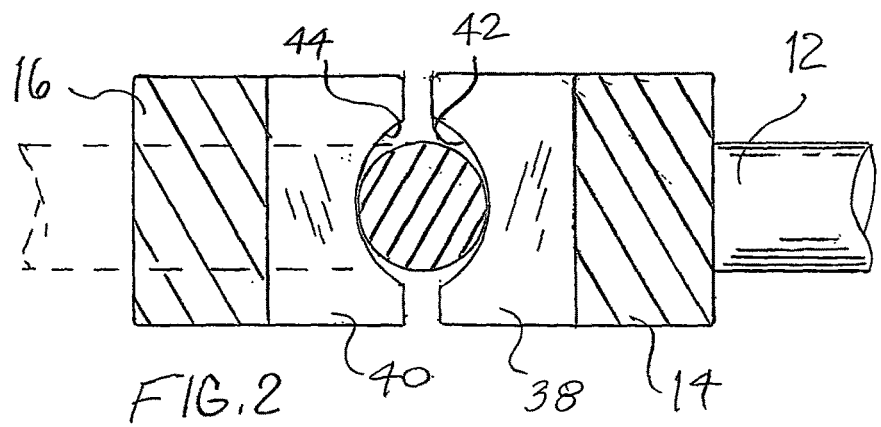
FIG. 2 is a sectional view taken along line 2-2 of FIG. 1.
Figure 3:
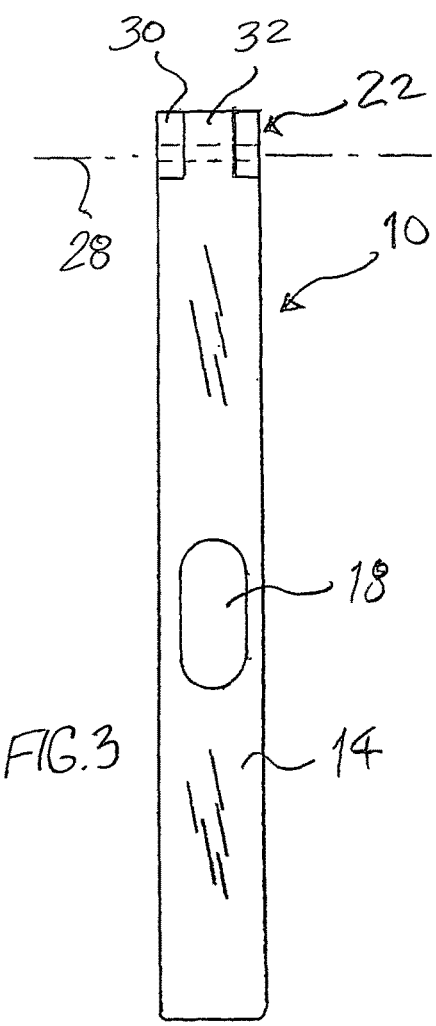
FIG. 3 is a right side elevational view of the device of FIG. 1.
Figure 4:
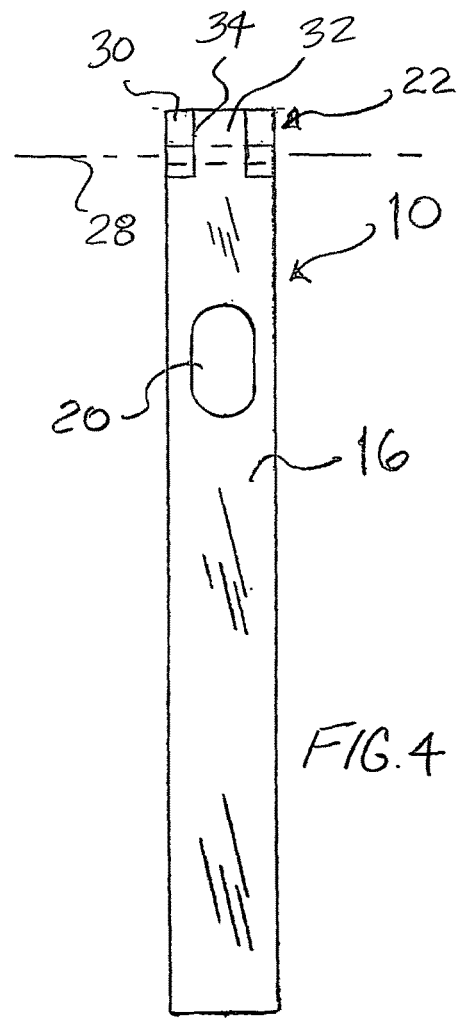
FIG. 4 is a left side elevational view of the device of FIG. 1.
Figure 5:
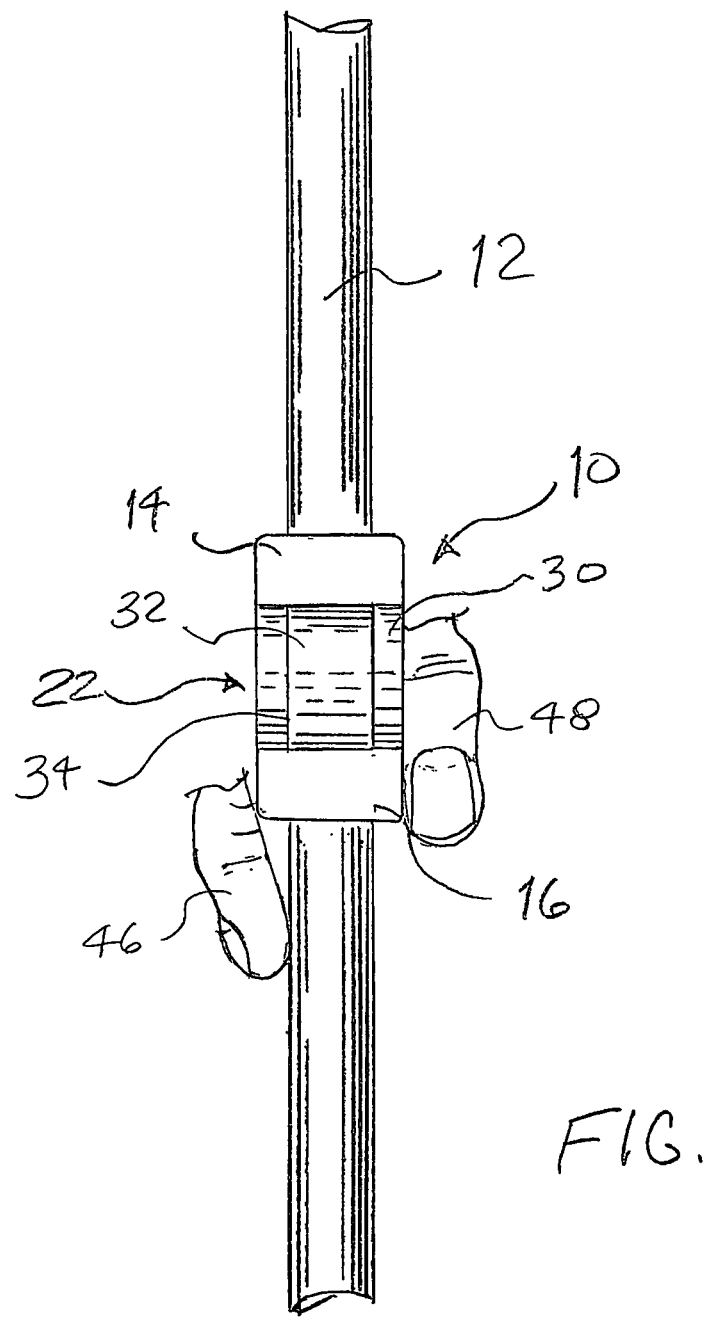
FIG. 5 is a top plan view of the device of FIG. 1, showing an endoscope tube in place and a portion of the practitioner's thumb and index finger.

In operation, endoscope insertion tube 12 is inserted within apertures 18 and 20 of arms 14 and 16, respectively, FIGS. 1, 2, and 5. Endoscope insertion tube also passes between jaws 38 and 40 of arms 14 and 16, respectively. Movement of arms 14 and 16 toward one another engages concave surfaces 42 and 44 with the outer surface of endoscope insertion tube 12 and prevents it from moving within apertures 18 and 20. With reference to FIG. 5, it may be observed that a secured grip is achieved with device 10 when arms 14 and 16 squeeze endoscope insertion tube 12. Such is the case, even though endoscope insertion tube 12 is lubricated. It should also be noted that jaws 38 and 40 are adaptable to different diameters of insertion tube 12. In essence, an ergonomic alignment of cable 12 with the forearm, wrist, and hand of the practitioner is achieved. Also, the rotation of endoscope insertion tube aligns with the rotation of the forearm of the practitioner, such that the wrist and hand of the practitioner lie in a position of comfort during use. Consequently, device 10 is held in a relaxed palm and index finger 46, FIG. 5. As shown in FIG. 5, index finger 46 is used as a pointer, while thumb 48 lies against device 10 when in use.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A gripping and holding device for an endoscopic insertion tube, comprising:
    a first arm having a proximal end and a distal end, the first arm having a first jaw and a first aperture, the first jaw located between the proximal and distal ends of the first arm, the first aperture formed in the first arm between the proximal end and the first jaw, the first aperture capable of passing the endoscopic insertion tube therethrough;
    a second arm substantially symmetrical in shape to the first arm, the second arm having a proximal end and a distal end, the second arm having a second jaw and a second aperture, the second jaw located between the proximal and distal ends of the second arm, the second aperture formed in the second arm between the second jaw and the distal end, the second aperture capable of passing the endoscopic insertion tube therethrough;
    wherein the first arm is hingedly connected to the second arm at the respective proximal ends such that the first jaw is capable of being moved towards the second jaw to grasp the endoscopic insertion tube between the first jaw and the second jaw at a point between the first aperture and the second aperture.

2. The device of claim 1 in which the first jaw comprises a protuberance possessing a concave surface.

3. The device of claim 2 in which the second jaw comprises a protuberance possessing a concave surface.

4. The device of claim 1 in which the first and second apertures are elongated.

5. The device of claim 4 in which the first jaw comprises a protuberance possessing a concave surface.

6. The device of claim 5 in which the second jaw comprises a protuberance possessing a concave surface.

7. The device of claim 1 wherein one of the first and second arms comprises a tongue at its proximal end, wherein the other of the first and second arms comprises slot at its proximal end, the tongue fitting within the slot to hingedly connect the first arm to the second arm.

8. The device of claim 7 in which the first and second apertures are elongated and the first aperture lies closer to the hinged connection than the second aperture.

9. The device of claim 8 in which the first jaw comprises a protuberance possessing a concave surface.

10. The device of claim 9 in which the second jaw comprises a protuberance possessing a concave surface.

\* \* \* \* \*